United States Patent [19]

Kawamura

[11] Patent Number: 4,877,967
[45] Date of Patent: Oct. 31, 1989

[54] PACKAGE INSPECTING APPARATUS

[75] Inventor: Shuzo Kawamura, Joyo, Japan

[73] Assignee: Murata Kikai Kabushiki Kaisha, Kyoto, Japan

[21] Appl. No.: 55,715

[22] Filed: May 28, 1987

[30] Foreign Application Priority Data

| Jun. 3, 1986 [JP] | Japan | 61-128413 |
| Jun. 6, 1986 [JP] | Japan | 61-86404[U] |
| Jun. 10, 1986 [JP] | Japan | 61-89159[U] |
| Jun. 13, 1986 [JP] | Japan | 61-90103[U] |

[51] Int. Cl.$^4$ .................................. G01N 21/64
[52] U.S. Cl. ........................ 250/461.1; 250/459.1
[58] Field of Search ............... 250/461.1, 459.1, 458.1, 250/372

[56] References Cited

U.S. PATENT DOCUMENTS 4,778,999 10/1988 Fisher ..................... 250/461.1

FOREIGN PATENT DOCUMENTS 0086743 5/1982 Japan ..................... 250/461.1

Primary Examiner—Janice A. Howell
Assistant Examiner—Richard Hanig
Attorney, Agent, or Firm—Spensley Horn Jubas & Lubitz

[57] ABSTRACT

An inspecting station for inspecting a package to find out whether or not it has a regular winding form or profile or it has different types of yarns wound thereon is located within a dark room in the form of a tunnel which is located intermediately of and covers a transporting path such as a belt conveyor for supplying packages to a subsequent step. A package inspecting device which uses an optical appliance is provided in the dark room.

2 Claims, 8 Drawing Sheets

PACKAGE INSPECTING APPARATUS

FIELD OF THE INVENTION AND RELATED ART STATEMENT

This invention relates to a package inspecting apparatus locating intermediately of a transporting path for inspecting a winding form or profile of a package, weight of a package and the like.

Packages wound up by a yarn winding device such as an automatic winder are then placed onto transport trays and supplied to a subsequent step by way of a transporting device such as a belt conveyor. However, packages may possibly be defective in winding form or profile such that there is a step in a layer of wound yarn or there are some convexes or concaves at a surface of an axial end portion of a layer of wound yarn which are caused by an eccentric winding pipe or by some other reasons, or the package is defective in that several yarns which are different in thickness, raw material or the like are wound on a single package. Since such defective packages may not easily be found out by mere observation of an operator, inspection of packages is usually performed using an optical appliance. In inspection by an optical appliance, for example, light is irradiated upon a surface of a layer of a wound yarn on a package, and reflected light is received by an image sensor in order to detect a condition of the surface of the yarn layer of the package. Accordingly, it is desirable to interrupt extraneous light which is useless to such inspection. Conventionally, to this end, an inspection station is located at a separate position outside a transporting path for packages, and packages are thus trasferred, using a lift or some other means, from the transporting path to the inspecting station at which the packages are then inspected.

Where a visible ray or an ultraviolet ray is irradiated upon a package and relfected light or fluorescent light is received to inspect a winding form or profile of the package, if such inspection is performed within a region within which external light is interrupted such as a dark room, the inspection accuracy can be improved. However, where inspection is performed at a separate place after packages have been transferred from a package transporting path as in the conventional arrangement described above, it is an inefficient use of space a factory and cost of equipment and further lost production efficiency.

Conventionally, inspection for the weight of packages is performed at a station for weight inspection provided in a path separate from a package transporting path because it is actually impossible for an operator to lift packages one by one to measure the weights of them. Thus, packages which are advanced along the package transporting path are mechanically introduced one by one into the separate path and to the station for weight inspection at which they are inspected for weight. Those of the packages which have passed the inspection are introduced again into the package transporting path.

The prior art wherein inspection of a package for weight is performed in a path separate from a package transporting path requires various equipment and factory including equipment for the separate path and an apparatus for transferring packages from the package transporting path to the separate path. Accordingly, the prior art is defective in ecomony.

OBJECT AND SUMMARY OF THE INVENTION

It is an object of the invention to propose a package inspecting apparatus which is constituted so as to allow efficient and accurate inspection by provision of an inspecting station for packages at an intermediate position of a transporting path provided for supplying packages wound by a winding device to a subsequent step.

According to the present invention, an inspecting station for inspecting a package to find out whether or not it has a regular winding form or profile or it has different types of yarns wound thereon is located within a dark room in the form of a tunnel which is located intermediately of and covers a transporting path such as a belt conveyor for supplying packages to a subsequent step. A light interrupting door is located at each of an entrance and an exit of the dark room and is opened and closed by a package passing the same. Thus, a package can be inspected with accuracy within the dark room without transferring the package to a separate place. A package inspecting device for inspecting a winding form of a package or for inspecting a lower end face of a package, which uses an optical appliance, is provided in the dark room.

Furthermore, an inspecting station for inspecting a package for weight may be located intermediately of a transporting path such as a belt conveyor which is provided for supplying a package to a subsequent next step.

DETAILED DESCRIPTION OF PREFERRED EMBODIMENTS

A package wound by a yarn winding device or the like is fed along the transporting path to the entrance of the dark room. After it has been confirmed that there is no package positioned in the dark room, the package advances into the dark room to the inspecting station whereupon it pushes open the light interrupting door at the entrance of the dark room. As the light interrupting door is thus released from the package, it is moved back to close the entrance of the dark room. At the inspecting station, the package is inspected for its winding form or profile and so on, and then after completion of such inspection, the package is advanced again. The package now pushes open the door at the exit of the dark room and is advanced to the next step. The door at the exit of the dark room is returned to shut the exit of the dark room when it is released from the package. Such a sequence of operations will be repeated to effect inspection of packages fed along the transporting path one after another for their winding form or profile.

Figure 1:
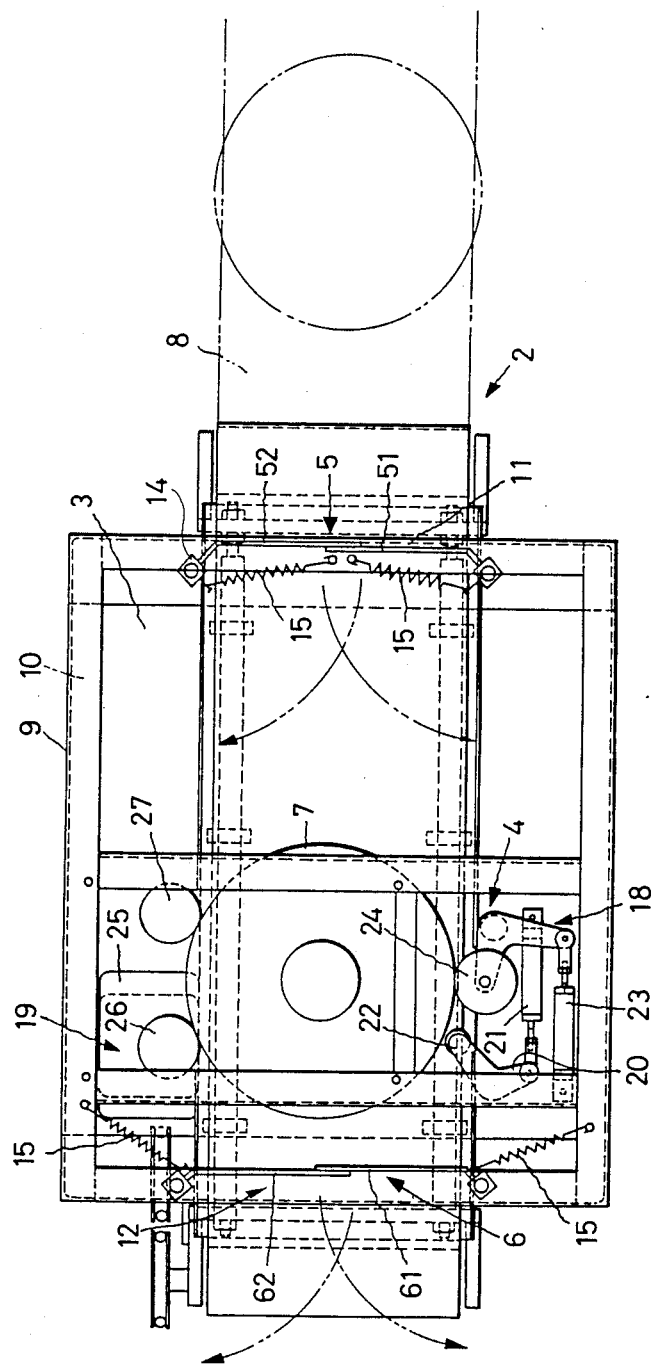
FIG. 1 is a horizontal sectional plan view of a package inspecting apparatus according to a first embodiment of the present invention.
Figure 2:
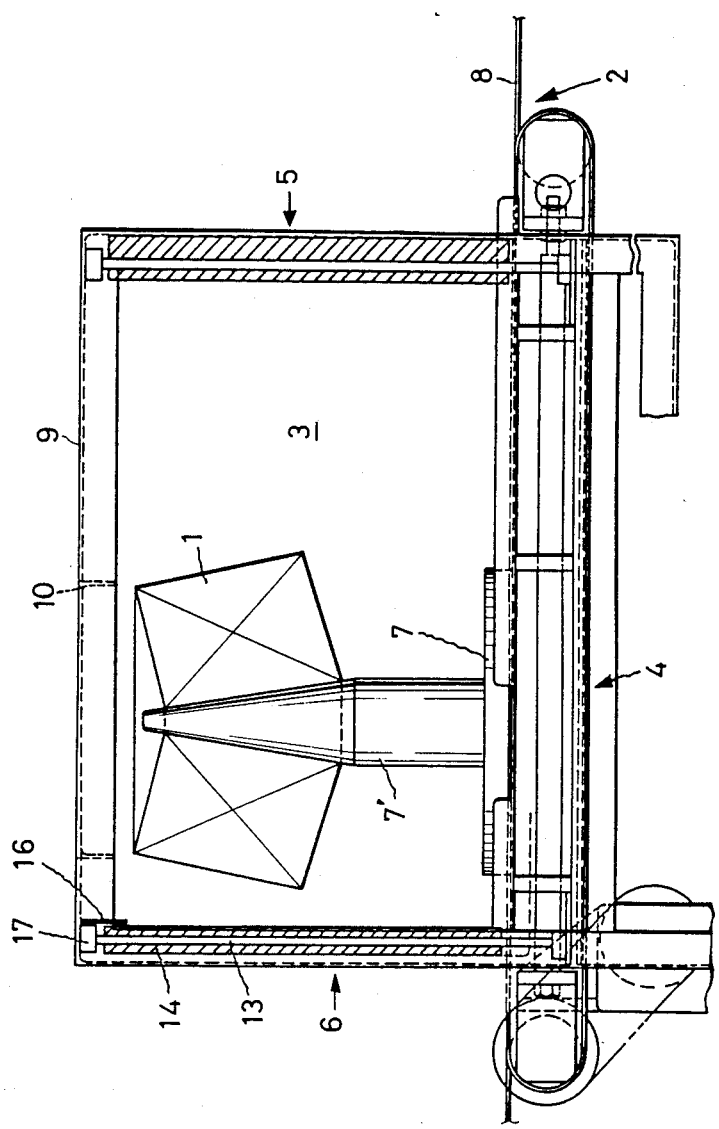
FIG. 2 is a vertical sectional front elevational view of the package inspecting apparatus of FIG. 1.

A first embodiment of a package inspecting apparatus of the present invention will now be described with reference to FIGS. 1 and 2.

A package inspecting apparatus according to the present invention includes a dark room 3 located intermediately of a transporting path 2 for a package 1, an inspecting station 4 located within the dark room 3, and a pair of light interrupting doors 5, 6 located at an entrance and an exit of the dark room 4, respectively.

A package 1 wound by a yarn winding device such as an automatic winder is supported on a transporting tray 7 and carried on a belt conveyor 8 to a subsequent next step as in the prior art described above. The dark room 3 is located at a suitable position of the belt conveyor 8 and is in the form of a tunnel including a light interrupting member 9 which covers opposite sides and an upper side of the belt conveyor 8 with respect to a direction of transportation of the belt conveyor 8. The light interrupting member 9 is secured to a frame 10 of equal-angle steel or the like by suitable means such as riveting. The light interrupting doors 5, 6 for closing opposite openings of the dark room 3 are located at an entrance 11 and an exit 12 of the tunnel-formed dark room 3. The light interrupting doors 5, 6 may each be a double-leafed hinged door which is pushed open by a transporting tray 7 being fed on the belt conveyor 8 and wherein a pair of left and right door plates 51, 52 or 61, 62 partly overlap each other when they are closed. The door plates 51, 52, 61, 62 are each supported on a support member 14 in the form of an angular post. Meanwhile, a shaft 13 extends between the floor and the ceiling portion of the frame 10 through a center through-hole of each of the support members 14 and is supported at each of opposite ends thereof by means of a bearing 17. Accordingly, the light interrupting doors 5, 6 are supported on the shafts 13 via the support members 14. A coil spring 15 extends between each of the support members 14 and the frame 10 so that the light interrupting doors 5, 6 pushed open by a package 1 may be individually closed by restoring forces of the associated coil springs 15. It is to be noted that the light interrupting door 5 at the entrance 11 is brought into contact with and stopped by a portion of the frame 10 when it is closed, but the light interrupting door 6 at the exit 12 is brought into contact with and stopped by a stopper 16 mounted on one of the upper bearings 17 and backed up by a portion of the frame 10. The light interrupting doors 5, 6 may not necessarily be of the type including door plates and may otherwise be of the type including a pair of curtains arranged in a partly overlapping relationship at mid portions thereof. Within the dark room 3 constituted in such a manner as described above, the inspecting station 4 is located. The inspecting station 4 includes a positioning mechanism 18 and a driving mechanism 19 for stopping and turning only a transporting tray 7 on the belt conveyor 8 being fed. The positioning mechanism 18 includes a movable member 20 which is moved back and forth by back and forth movement of a piston 21 to move an arm 22 thereof into and out of a passage of movement of a transporting tray 7, and a pressing member 24 which is moved, when the movable member 20 is contacted by a transporting tray 7, by a piston 23 to press the transporting tray 7 in a direction perpendicular to the direction of movement of the belt conveyor 8 against the driving mechanism 19. Meanwhile, the driving mechanism 19 includes a rotary member 26 mounted on a rotary shaft of a motor 25 so that a transporting tray 7 may be rotated by a turning force of the rotary member 26. A rotatable driven member 27 is also provided so that a tranporting tray 7 may be supported at three points thereof and held from displacement by the pressing member 24, rotary member 26 and driven member 27. It is to be noted that an inspecting device is of the type wherein a visible ray emitted from a halogen lamp and an ultraviolet ray emitted from a black light are both irradiated upon a package and reflected light and fluorescent light then are received by light receivers or the like to detect an extraordinary condition of the package, and while the inspecting device is not shown in the present embodiment, it may be located contiguously to a ceiling portion of the dark room 3.

Now, operation of a package inspecting apparatus of the present invention will be described in detail with reference to the embodiment described above.

A package 1 wound by a yarn winding device not shown is supported on a peg 7' erected at the center of a transporting tray 7 and is fed on the belt conveyor 8. The transporting tray 7 on which the package 1 is supported soon comes to the dark room 3, and in case another transporting tray is positioned within the dark room 3, the transporting tray 7 is stopped from further movement by a stopping mechanism not shown. When it is confirmed that there is no transporting tray 7 positioned within the dark room 3, the transporting tray 7 is admitted into the dark room 3 on the belt conveyor 8 while pushing open the light interrupting door 5 at the entrance 11 of the dark room 3. As the transporting tray 7 is moved away from the door plates 51, 52 of the light interrupting door 5, the door plates 51, 52 are pivoted back to close the entrance 11 of the dark room 3 by restoring forces of the respective coil springs 15. The transporting tray 7 admitted in the dark room 3 and supporting the package 1 thereon then arrives at the inspecting station 4. After the transporting tray 7 has thus been supplied to the inspecting station 4 while the arm 22 of the movable member 20 is positioned within the passage of movement of the transporting tray 7 with the movable member 20 pulled by the piston 21, the transporting tray 7 abuts with the arm 22 of the movable member 20 as it further advances. Thereupon, the piston 23 pushes out the pressing member 24 to push the transporting tray 7 to slide in a direction perpendicular to the direction of movement of the belt conveyor 8. The thus slid transporting tray 7 is then pressed by the rotary member 26 and the driven member 27 and receives a turning force of the rotary member 26 which is driven by the motor 25 so that the transporting tray 7 is rotated continuously or intermittently by the rotary member 26. Consequently, the package 1 on the transporting tray 7 is also rotated. Then, a visible ray and an ultraviolet ray are irradiated upon the rotating package 1 from the optical appliances not shown in order to effect predetermined inspection of the package 1. In the meantime, the belt conveyor 8 continues its movement. After completion of the intended inspection, the pressing member 24 and the arm 22 of the movable member 20 are retracted individually to allow the transporting tray 7 to be fed toward the exit 12 of the dark room 3 as the belt conveyor 8 moves. Then, the transporting tray 7 is further advanced while pushing open the door plates 61, 62 of the light interrupting door 6 at the exit 12 of the dark room 3 and is then supplied to the subsequent step. As the tray 7 is moved away from the door plates 61, 62, the door plates 61, 62 are pivoted back by restoring forces of the respective coil springs 15 until they are contacted with the stopper 16 and stopped by the frame 10, and consequently the exit 12 of the dark room 3 is closed by the light interrupting door 6. After then, another package on a transporting tray will be admitted into the dark room 3 in order to repeat such an inspecting operation as described above.

A package inspecting apparatus according to the first embodiment of the present invention comprises a dark room in the form of a tunnel which is located intermediately of and covers a transporting path for feeding a package to a next step, and a light interrupting door which is located at each of an entrance and an exit of the dark room and is opened and closed as a packages passes it. Accordingly, the dark room located intermediately of the transporting path prevents a possible interference with inspection of a package. Thus, the package inspecting apparatus allows accurate and efficient inspection of a package by a simple and economic equipment.

Figure 3:
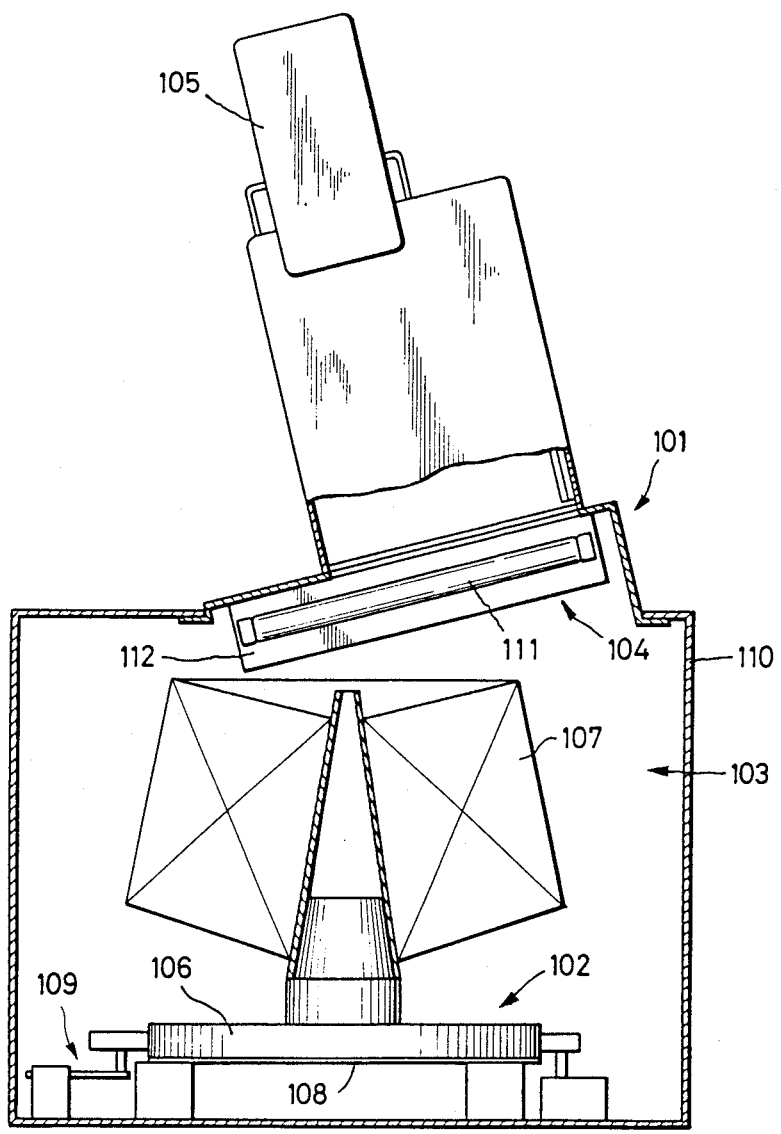
FIG. 3 is a vertical sectional front elevational view of a second embodiment of a package inspecting apparatus.
Figure 4:
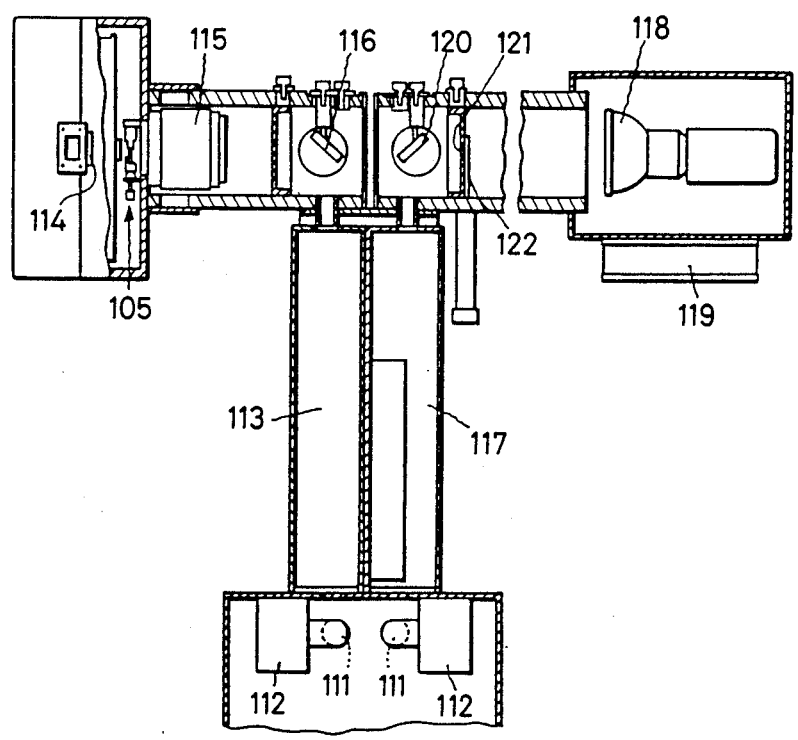
FIG. 4 is a vertical sectional side elevational view of a major part showing an embodiment wherein a wound yarn form inspecting apparatus is combined with a package inspecting apparatus.

Now, a second embodiment of a package inspecting apparatus of the present invention for inspecting a wound yarn form of a package with reference to FIGS. 3 and 4.

A package inspecting apparatus 101 according to the present invention includes an inspecting station 102, a dark room 103, and an ultraviolet ray generator 104 and a light receiver 105.

The inspecting station 102 is located within the dark room 103 and includes a conveyor 108 for transporting a tray 106 which supports a package 107 produced by a yarn winding device not shown and receiving the tray 106 thereon, and a driving mechanism 109 for positioning and turning the tray 106. The dark room 103 is formed by a light interrupting member 110 which covers upper and lower sides and the remaining four sides of the inspecting station 102, and an ultraviolet ray generator 104 is located at the top wall of the dark room 103. The ultraviolet ray generator 104 includes two black lights 111 as light sources supported in an opposing relationship on a support member 112 and each including a mercury-arc lamp and a filter in combination. A light introducing path 113 for introducing fluoroscent light emitted from a package 107 is located in a contiguous relationship to and above the ultraviolet ray generator 104, and the light receiver 105 for receiving fluorescent light is mounted in the light introducing path 113.

It is to be noted that a device for inspecting a wound yarn form of a package is also provided in an integral relationship to the apparatus of the present invention. Thus, a solid state image pickup element 114 for image inspection is provided for the light receiver 105 while a lens 115 and a reflecting mirror 116 are located within the light introducing path 113. A lighting path 117 is located in a back to back relationship to the light introducing path 113, and a halogen lamp 118 is mounted as a light source in a contiguous relationship to the lighting path 117. Reference numeral 119 denotes a cooling fan, and 120 a reflecting mirror, and a shutter 122 is also provided for closing a light inlet port 121 which is in turn provided for admitting a visible ray when inspection with an ultraviolet ray is to be effected.

Now, operation of a package inspecting apparatus according to the present invention will be described in detail with reference to the embodiment described above.

A package 107 supported on a tray 106 is introduced into the dark room 103 via a transporting path not shown and is placed onto the conveyor 108 at the inspecting station 102. The package 107 is turned by the driving mechanism 109. Then, the light inlet port 121 is closed with the shutter 122 and a switch of the ultraviolet ray generator 104 is turned on. Consequently, an ultraviolet ray is emitted from the back light 111 and is irradiated upon a surface of the package 107. Thus, a yarn which form the package 107 absorbs the ultraviolet ray and emits the thus absorbed energy as fluorescent light. The fluorescent light is introduced along the light introducing path 113, reflected by the reflecting mirror 116, condensed by the lens 115 and finally received by the light receiver 105. A yarn has a characteristic that the amount of fluorescent light emitted therefrom varies depending upon its type of raw material, thickness and so on, and where a package includes a yarn of a single type, the amount of fluorescent light emitted in response to an ultraviolet ray irradiated upon a rotating package will normally be uniform. Accordingly, if the light receiver 105 detects emission of an uniform amount of fluorescent light, then it is found out that the package inspected is an ordinary one. In this case, the shutter 122 is subsequently opened and the halogen lamp 118 is lit to emit a visible light therefrom. The visible ray is then passed through the light inlet port 121 and reflected by the reflecting mirror 120 and finally irradiated upon the surface of the package 107. The light is thus reflected by the surface of the package 107, passed through the light introducing path 113, reflected by the reflecting mirror 116, condensed by the lens 115, and finally received by the solid state image pickup element 114 in order to inspect the wound yarn form of the package 107.

It is to be noted that inspection of a package by irradiation of an ultraviolet ray may be performed with the shutter closed alternatively after completion of inspection of a wound yarn form of the package.

To the contrary, where the package 107 includes yarns of two different types which are different in thickness, if an ultraviolet ray is irradiated upon the package 107, the amount of fluorescent light emitted from the yarns will vary irregularly as the package rotates, and accordingly the light receiver 105 will detect the extraordinary fluorescent light is being emitted from the package. In other words, the light receiver 105 will detect that the package includes yarns of different types wound thereon. The package which is determined as an extraordinary one as a result of the inspection will be removed from the transporting line.

A package inspecting apparatus 101 according to the present invention is constituted such that a package is introduced into an inspecting station within a dark room and an ultraviolet ray is irradiated upon the package to cause a yarn or yarns wound on the package to emit fluorescent light the amount of which is detected by a light receiver. Accordingly, if the package includes yarns of two or more different types wound thereon, it will be automatically found out as an extraordinary package. Thus, if the package inspecting apparatus is combined with a wound yarn package form inspecting apparatus which utilizes a visible ray, all the necessary inspections of a package can be performed at a location.

Now, another embodiment for inspecting of a lower end face of a package will be illustrated.

Inspection of a lower end face of a package is performed at a position intermediately of a transporting path such as a belt conveyor which is provided for supplying a package to a subsequent next step. To this end, a turning device for stopping a package advanced thereto and for turning the package is located at a suitable position of the belt conveyor. Meanwhile, inspection of a package for yarn winding form and so on is effected by means of an optical appliance. To this end, inspecting appliances including a light source for projecting a visible ray toward a lower end face of a package being turned, a light receiver for picking up light reflected from the lower end face of the package, and an analyzer for analyzing light information obtained by the light receiver are located in the neighborhood of the turning device.

Accordingly, a package wound by a yarn winding device or the like is fed along the transporting path to the next step and soon reaches an inspecting position. When the package is positioned on the turning device, the package is turned by a rotary member which is rotated by a motor. At the same time, light is projected from the light source toward a lower end face of the package and reflected by the latter. The reflected light is picked up by the light receiver and analyzed by the analyzer such as an image sensor to inspect a yarn winding form or the like of the package. After completion of the inspection, the package is returned to the transporting path so that it may subsequently be fed to the next step.

Figure 5:
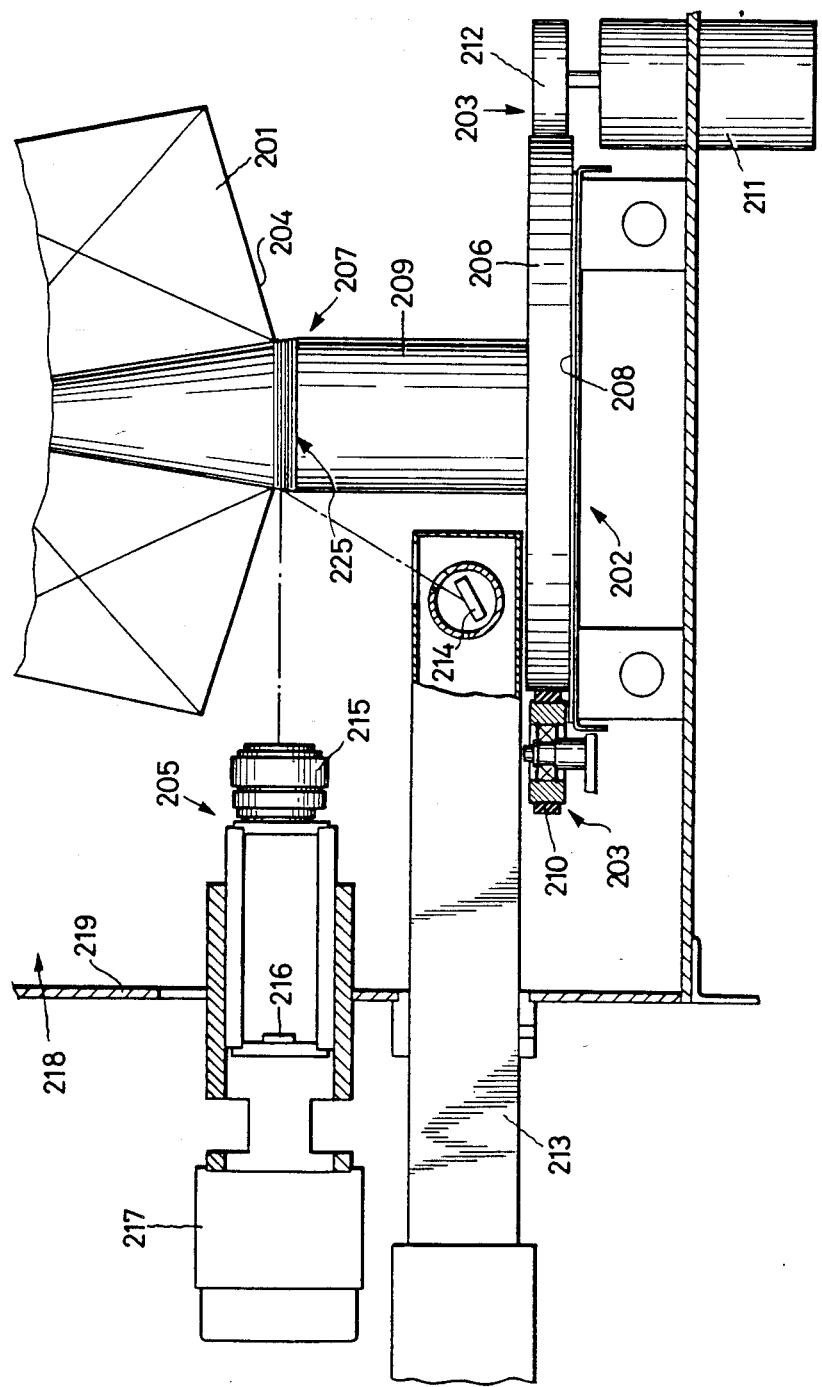
FIG. 5 is a vertical sectional front elevational view showing a third embodiment of an apparatus for inspecting a lower end face of a package according to the present invention together with a manner in which it is used.

Now, embodiments of an apparatus for inspecting a lower end face of a package according to the present invention will be described with reference to FIGS. 5 and 6.

A third embodiment of an apparatus for inspecting a lower end face of a package according to the present invention comprises a turning device 203 located in a transporting path 202 for a package 201, and an inspecting device 205 also located in the transporting path 202 for projecting light to a lower end face 204 of the package 201 to inspect whether a yarn winding form of the package 201 is good or not.

A package 201 is wound by a yarn winding device such as an automatic winder, then uprightly fitted on a peg 207 of a transporting tray 206, and fed on a belt conveyor 208 along the transporting path 202, similarly as in the prior art. However, according to this embodiment, the peg 207 of the transporting tray 206 is elongated at its root portion 209 thereof so that a package 201 may be uprightly fitted and held at a higher position on the peg 207. The turning device 203 for a package 201 is located at a suitable position of the transporting path 202. The turning device 203 includes a pressure roller 210 for stopping a transporting tray 206 from further advancement while the belt conveyor 208 continues its circulating movement and for pressing the transporting tray 206 in a direction of the width of the belt conveyor 208, and a rotary member 212 for receiving the transporting tray 206 pressed by the pressure roller 210 and for rotating the transporting tray 206 as it is rotated by a motor 211. The inspecting device 205 includes a light source such as a halogen lamp not shown, a light projecting means including a light introducing path 213 for introducing light from the light source to a lower bunch winding 225 of a package 201 and a reflecting mirror 214 mounted for adjustment to a selected angular position for projecting light introduced by the light introducing path 213 accurately to a preset position of the lower end face 204 of the package 201, and a light receiving means including a lens 215 and a solid state image pickup element 216 for receiving light reflected from the lower bunch winding 225 of the package 201 and an analyzer 217 for analyzing data picked up by the solid state image pickup element 216 to determine whether or not the article inspected is allowable. Principal parts of the turning device 203 and the inspecting device 205 are accommodated within a dark room 218 which is formed by a light interrupting member 219 which covers the transporting path 202. In the example shown, the lens 215 is directed toward a bunch winding portion of a package 201, but it will be appreciated that the position and the direction of the lens 215 can be adjusted suitably by a mechanism not shown.

Figure 6:
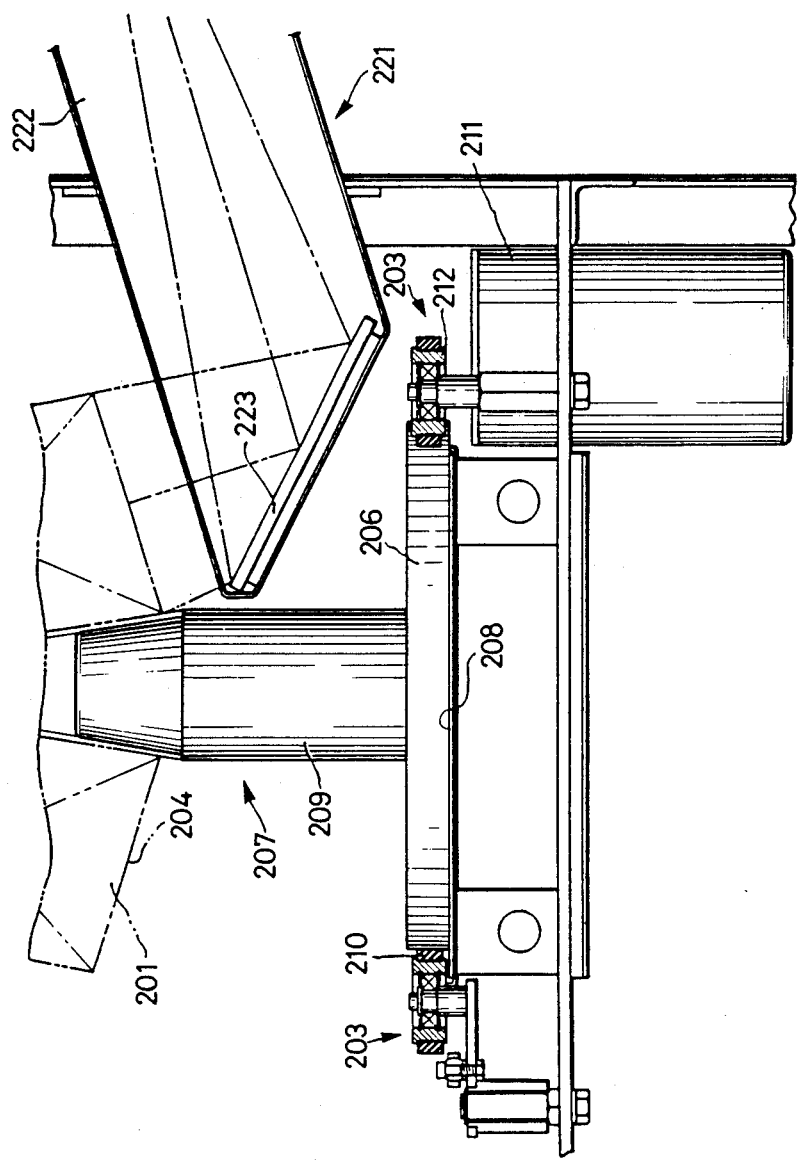
FIG. 6 is a vertical sectional front elevational view showing a fourth embodiment together with a manner in which it is used.

FIG. 6 shows a fourth embodiment of an inspecting device, and in FIG. 6, like parts or elements are denoted by like reference numerals to those of the third embodiment because the remaining mechanisms except the inspecting device 221 is similar to those of the third embodiment.

The inspecting device 221 includes a light introducing path 222 extending into a dark room 218, and a reflecting mirror 223 located at an end portion of the light introducing path 222 for directing light projected from a light source not shown toward a lower end face 204 of a package 201 and for receiving light reflected from the lower end face 204 of the package 201 to introduce the same to a light receiving device not shown via the same light introducing path 222.

Now, operation of an apparatus for inspecting a lower end face of a package will be described with reference to the third embodiment described above.

A package 201 wound up by a yarn winding device not shown is fitted uprightly on the peg 207 of a transporting tray 206, and the transporting tray 206 is fed on the belt conveyor 208 along the transporting path 202. When the package 201 arrives at the dark room 218 and it is confirmed that no other package 201 is accommodated and inspected within the dark room 218, the package 201 is admitted into the dark room 218 and thus arrives at the turning device 203. Here, the transporting tray 206 is stopped from further advancement by a stopping mechanism not shown, and at the same time the pressure roller 210 of the turning device 203 is operated to push out the transporting tray 206 in a direction of the width of the belt conveyor 208, that is, in a rightward direction in FIG. 6, and further press the transporting tray 206 against the rotary member 212. The rotary member 212 is rotated as the motor is energized so that the transporting tray 206 is rotated by a turning force of the rotary member 212 and consequently the package 201 is rotated in an integral relationship by the transporting tray 206. Meanwhile, as light is projected from the light source not shown, the light is introduced by the light introducing path 213, then reflected by the reflecting mirror 214 and irradiated upon the lower bunch winding portion 225 of the package 201. The light is then reflected by the lower bunch winding 225 of the package 201 and condensed by the lens 215 and picked up by the solid state image pickup element 216. The image thus picked up by the element 216 is analyzed by the analyzer 217 in order to determine whether or not the article is allowable.

After completion of the intended inspection, the pressure roller 210 is retracted so that the transporting tray 206 is subsequently supplied to the next step as the belt conveyor 208 is advanced. Such a sequence of operations as described above will be repeated in order to successively effect inspection of lower end faces of packages.

An apparatus for inspecting a lower end face of a package according to these embodiments is located intermediately of a transporting path which is provided for feeding a package to a subsequent next step. Accordingly, there is no necessity of provision of an additional separate transporting path in which inspection is to be performed, and accordingly the apparatus is economical. Besides, a time for transporation of a package can be reduced, and efficient and accurate inspection can be allowed.

Figure 7:
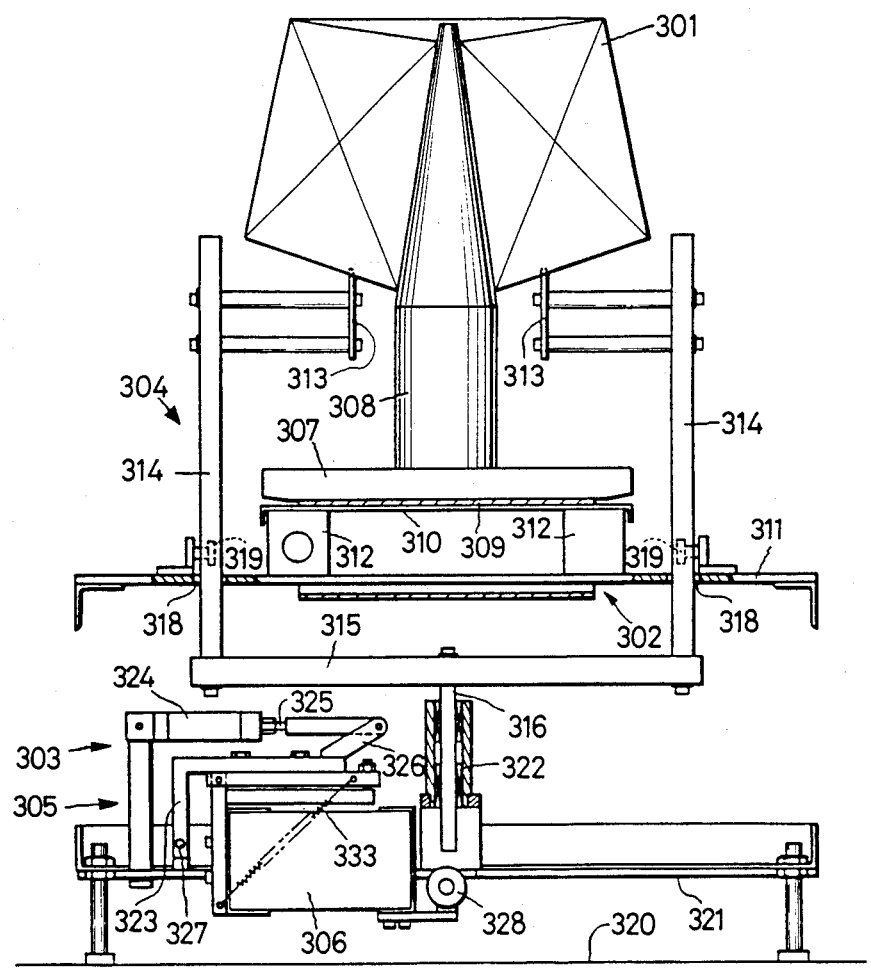
FIG. 7 is a front elevational view showing a package weight inspecting device according to the present invention when it is in use.
Figure 9:
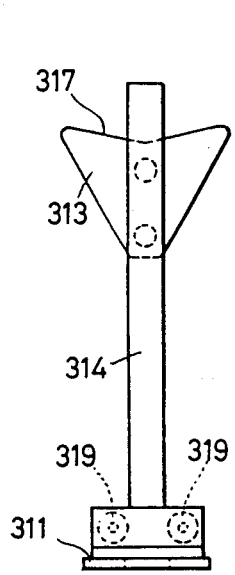
FIG. 9 is a side elevational view of a supporting device.
Figure 8:
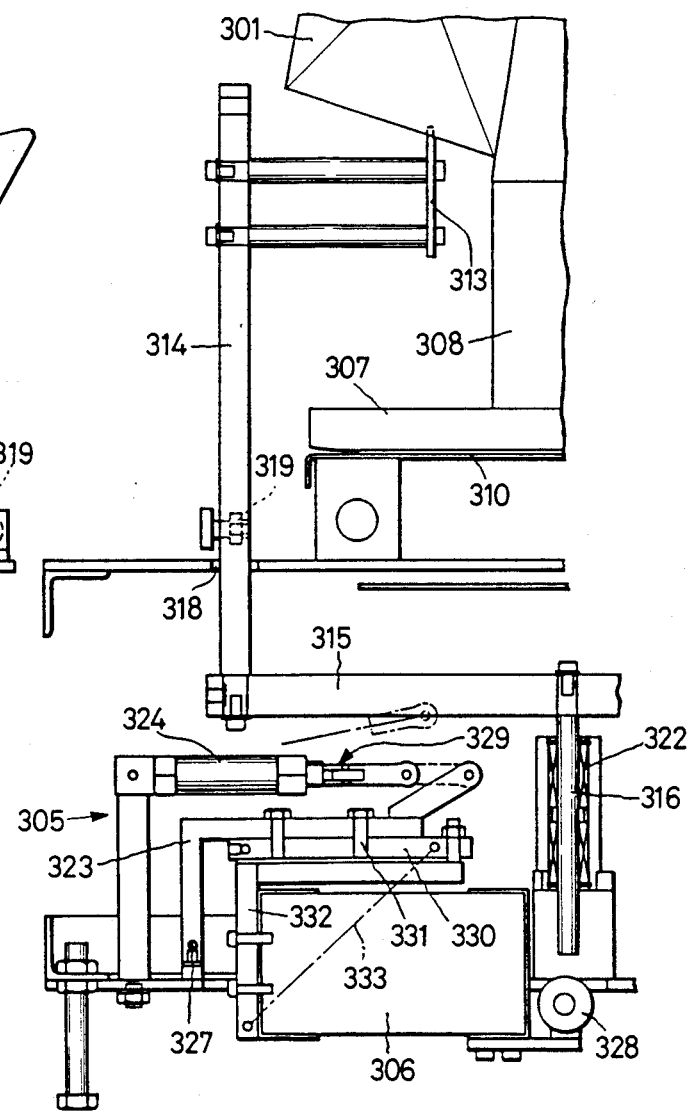
FIG. 8 is a vertical sectional front elevational view of part of the package weight inspecting apparatus of FIG. 7.

Further embodiment of the present invention will be illustrated referring to FIGS. 7 to 9.

An inspecting station for inspecting a package for weight is located intermediately of a transporting path such as a belt conveyor which is provided for supplying a package to a subsequent next step. The inspecting station includes a package supporting device and a driving mechanism for the package supporting device, and a weight measuring instrument which measures a weight of a package from a balanced condition between the supporting device on which a package is carried and the driving mechanism on which the supporting device is held. Thus, when a package reaches the inspecting station, the driving mechanism operates to lift the supporting device to lift the package so that movement of the package which is advanced along the transporting path may not undergo such an interference that the package strikes against the supporting device. When the package is lifted in this manner, a strain between a load applied to the supporting device and a force which lifts the supporting device is measured by the weight measuring instrument to detect a weight of the package.

A package wound by a yarn winding device or the like is fed along the transporting path to the next step and soon reaches the weight inspecting station. When the package is positioned at a predetermined location, the driving mechanism for the supporting device operates to lift the supporting device. As the supporting device is lifted, the package is gradually lifted thereby until the lifting movement of the supporting device is stopped at a predetermined position. Thereupon, the supporting device on which the package is carried and the driving mechanism which holds the supporting device to the predetermined position are well balanced with each other, and this condition is measured by the weight measuring instrument to detect a weight of the package. After completion of the weight inspection, the driving mechanism operates again to lower the supporting device to return the package to the transporting path, whereafter the supporting device is further lowered until a position is reached at which it will not interfere with subsequence advancement of the package. The package returned to the transporting path is then advanced to the subsequent next step while another next package will be supplied to the inspecting station. Such a sequence of operations will be repeated to effect inspection of packages for weight intermediately of the transporting path.

Now, an embodiment of a package weight inspecting apparatus according to the present invention will be described with reference to the drawings.

A package weight inspecting apparatus according to the present invention includes a weight inspecting station 303 located intermediatly of a transporting path 302 for a package 301. The weight inspecting station 303 includes a supporting device 304 for lifting a package 301, a driving mechanism 305 for the supporting device 304, and a weight measuring instrument 306 located between the supporting device 304 and the driving mechanism 305.

A package 301 is wound into a shape of a piece of cheese or some other shape by a yarn winding device such as an automatic winder, then carried on a peg 308 of a transporting tray 307, and fed to a subsequent next step along the transporting path 302, similarly as in the prior art. The transporting path 302 along which the package 301 is fed may include an endless annular belt 309 mounted for circulating movement along a plate 310 which is supported on a plate base 311 by means of a plurality of supporting members 312.

The weight inspecting station 303 is located at a suitable position of the transporting path 302. The supporting device 304 for lifting a package 301 includes a pair of supporting members 313, a pair of support posts 314 for supporting the supporting members 313 thereon, a connecting member 315 for interconnecting the support posts 314, and a main posts 316 for supporting the connecting member 315 at a central portion. The supporting members 313 each have an upper edge 317 concaved arcuately as seen in FIG. 9 and are supported on the support posts 314 which extend uprightly on opposite sides of the belt 309 through the plate base 311. The support posts 314 are mounted for up and down movement under the guidance of a pair of guide rollers 319 located adjacent a pair of support post fitting holes 318 formed in the plate base 311. The main post 316 is fitted in a bearing 322 erected on a base plate 321 mounted on a floor 320 such that the supporting device 304 before measurement may have the connecting member 315 thereof supported by an upper face of the bearing 322. The driving mechanism 305 for the supporting device 304 is located on the base plate 321. The driving mechanism 305 includes an inverted L-shaped rockable arm 323 supported for rockable motion on the base plate 321, and a cylinder 324 having a rod 325 connected to the rockable arm 323 by way of a connecting member 326, whereby as the rod 325 of the cylinder 324 makes a reciprocal motion, the rockable arm 323 is rocked around a support shaft 327 thereof. The rockable arm 323 carries thereon the weight measuring instrument 306 on which a pressure roller 328 is mounted. Accordingly, as the weight measuring instrument 306 is rocked by a rocking motion of the rockable member 323, the pressure roller 328 makes a rocking motion in an integral relationship with the weight measuring instrument 306 to push up the main post 316 of the supporting device 304. The weight measuring instrument 306 measures a weight of a package 301 from an amount of its strain in a condition wherein a force of the rockable arm 323 to push up the supporting device 304 and a load applied to the supporting device 304 are well balanced with each other.

It is to be noted that since the amount of rocking movement of the rockable arm 323 is proportional to the amount of back and forth movement of the cylinder rod 325, a package, for example, of a conical shape to be inspected can be removed from the peg of a transporting tray only if it is lifted a little distance, and accordingly a collar 329 may be fitted on the rod 325 to control the amount of movement of the rockable member 323.

Meanwhile, if the rockable arm 323 is rocked to compulsorily rock the weight measuring instrument 306 when an excessive pressure is applied to the pressure roller 328 so that there is an obstacle to lifting movement of the pressure roller 328, there is the possibility that the weight measuring instrument 306 may be destroyed, and accordingly it is preferable to provide a destruction preventing mechanism between the weight measuring instrument 306 and the rockable arm 323. In the present embodiment, the destruction preventing mechanism includes a plate-formed member 330 secured integrally to the rockable arm 323, a holding member 332 supported for rocking motion on the plate-formed member 330 for holding the weight measuring instrument 306 thereon, and a spring 333 extending between the holding member 332 and the plate-formed member 330 for absorbing such a compulsory rocking motion of the rockable arm 323.

Operation of a package weight inspecting apparatus will now be described in detail with reference to the embodiment described above.

A package 301 wound up by a yarn winding device not shown is fitted uprightly on the peg 308 of a transporting tray 307, and the tray 307 is fed on the belt 309 along the transporting path 302. When the package 301 arrives at the weight inspecting station 303, the transporting tray 307 is stopped from further advancement by a stopping mechanism not shown. Then, the cylinder 324 is operated to move the rod 325 in a retreating direction. Thereupon, the rockable arm 323 is rocked in a counterclockwise direction in FIG. 7 around the support shaft 327 until a position as shown in phantom in FIG. 8 is reached. As the rockable arm 323 is rocked in this manner, the weight measuring instrument 306 is also rocked in the counterclockwise direction in FIG. 7 so that the pressure roller 328 mounted on the weight measuring instrument 306 is lifted to push up the main post 316 of the supporting device 304 to lift the supporting device 304. The supporting members 313 of the supporting device 304 are soon contacted with lower portions of the package 301 and lift the package 301 as they are further pushed up.

When the package 301 is lifted to a position at which it is completely removed from the peg 308 of the transporting tray 307, the motion to lift the supporting device 304 is stopped, and this position is measured by the weight measuring instrument 306. After completion of measurement of a weight of the package 301, the cylinder 324 operates to now push out the rod 325 thereof to rock the rockable arm 323 in a clockwise direction to return the weight measuring instrument 306 to its initial position before measurement. Thereupon, the pressure roller 328 is lowered to lower the supporting device 304 together with the package 301 until the package 301 is fitted on and supported by the peg 308 of the transporting tray 307. Still after then, the supporting device 304 is further lowered until the supporting members 313 reaches a position at which they do not interfere with subsequent transportation of the package 301. Such a sequence of operations as described above will be repeated in order to effect inspection of packages for weight.

A package weight inspecting apparatus according to the present invention comprises a weight inspecting station located intermediately of a transporting path which is provided for feeding a package to a subsequent next step. Accordingly, such possible losses in economy and time that may result from provision of an additional separate transporting path for packages as in the prior art arrangement can be eliminated, and accordingly, efficient inspection for weight can be allowed.

What is claimed is:

1. A package inspecting apparatus, comprising a package inspecting station, a dark room including a light interrupting member for covering said package inspecting station, an ultraviolet ray generator located within said dark room for irradiating an ultraviolet ray upon a surface of a package within said dark room, and a light receiver located in a contiguous relationship to said dark room for receiving fluorescent light emitted from the package which receives and absorbs an ultraviolet ray from said ultraviolet ray generator.

2. A package inspecting apparatus comprising:
 a package inspecting station,
 a dark room including a light interrupting member for covering the package inspecting station,
 an ultraviolet ray generator located within the dark room for irradiating an ultraviolet ray upon a surface of a package within the dark room, and
 a light receiver located in a contiguous relationship to the dark room for receiving fluorescent light emitted from the package which receives and absorbs an ultraviolet ray from the ultraviolet ray generator, wherein the light receiver further includes
 a solid state image pickup element for image inspection,
 a hloagen lamp as a light source, and
 a shutter device for closing a light inlet port for admitting a visible ray when inspection with an ultraviolet ray is to be effected.

* * * * *